(12) United States Patent
Matsufuji et al.

(10) Patent No.: US 11,020,338 B2
(45) Date of Patent: Jun. 1, 2021

(54) COMPOSITE PARTICLE AND PREPARATION THEREOF

(71) Applicant: L'OREAL, Paris (FR)

(72) Inventors: Shinichi Matsufuji, Kawasaki (JP); Toshifumi Shiroya, Kawasaki (JP); Christophe Dumousseaux, Kawasaki (JP); Andres Cardozo Perez, Le Thillay (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 15/536,165

(22) PCT Filed: Dec. 17, 2015

(86) PCT No.: PCT/JP2015/086148
§ 371 (c)(1),
(2) Date: Jun. 15, 2017

(87) PCT Pub. No.: WO2016/098910
PCT Pub. Date: Jun. 23, 2016

(65) Prior Publication Data
US 2017/0319458 A1    Nov. 9, 2017

(30) Foreign Application Priority Data
Dec. 17, 2014  (JP) .............................. JP2014-254742

(51) Int. Cl.
| | |
|---|---|
| *A61K 8/81* | (2006.01) |
| *A61K 8/73* | (2006.01) |
| *A61K 8/06* | (2006.01) |
| *A61K 8/02* | (2006.01) |
| *A61Q 1/00* | (2006.01) |
| *A61K 8/11* | (2006.01) |
| *A61K 8/29* | (2006.01) |
| *A61Q 19/00* | (2006.01) |
| *C08L 1/02* | (2006.01) |
| *C08L 33/12* | (2006.01) |

(52) U.S. Cl.
CPC .......... *A61K 8/8152* (2013.01); *A61K 8/0266* (2013.01); *A61K 8/062* (2013.01); *A61K 8/11* (2013.01); *A61K 8/29* (2013.01); *A61K 8/731* (2013.01); *A61K 8/8117* (2013.01); *A61K 8/8147* (2013.01); *A61Q 1/00* (2013.01); *A61Q 19/00* (2013.01); *C08L 1/02* (2013.01); *C08L 33/12* (2013.01); *A61K 2800/262* (2013.01); *A61K 2800/412* (2013.01); *A61K 2800/594* (2013.01); *A61K 2800/614* (2013.01); *A61K 2800/624* (2013.01); *A61K 2800/651* (2013.01); *A61K 2800/654* (2013.01); *C08L 2207/53* (2013.01)

(58) Field of Classification Search
None
See application file for complete search history.

(56) References Cited

U.S. PATENT DOCUMENTS

| | | | |
|---|---|---|---|
| 4,133,784 A | 1/1979 | Otey et al. | |
| 4,806,358 A * | 2/1989 | Khan | A61K 9/0007 424/466 |
| 5,262,458 A | 11/1993 | Bastioli et al. | |
| 5,374,452 A * | 12/1994 | Meybeck | A61K 9/1676 427/212 |
| 2005/0129638 A1* | 6/2005 | Dumousseaux | A61K 8/29 424/63 |
| 2007/0104662 A1* | 5/2007 | Satonaka | A61K 8/02 424/59 |
| 2009/0022791 A1* | 1/2009 | Obae | A61K 9/2018 424/464 |

FOREIGN PATENT DOCUMENTS

| | | |
|---|---|---|
| EP | 0327199 A2 | 8/1989 |
| JP | S63-110261 A | 5/1988 |
| JP | H03-99008 A | 4/1991 |
| JP | 05-220375 A | 8/1993 |
| JP | 2925728 B2 | 7/1999 |
| JP | 2004-514504 A | 5/2004 |
| JP | 2011-083753 A | 4/2011 |
| JP | 2011083753 A | 4/2011 |
| JP | 2013-534561 A | 9/2013 |
| JP | 2014-511397 A | 5/2014 |

(Continued)

OTHER PUBLICATIONS

Soh et al., "Importance of Small Pores in Microcrystalline Cellulose for Controlling Water Distribution during Extrusion-Spheronization," AAPS PharmSciTech, Vo. 9, No. 3, Sep. 2008, pp. 972-981 (Year: 2008).*
Thoorens et al., "Microcrystalline cellulose, a direct compression binder in a quality by design environment—A review," International Journal of Pharmaceutics 473 (2014) 64-72 (Year: 2014).*
International Search Report for PCT/JP2015/086148, dated Mar. 30, 2016.
Japanese Office Action for counterpart Application No. 2017-531921, dated Sep. 3, 2018 with translation.
Japanese Office Action for counterpart Application No. 2017-531921, dated Mar. 25, 2019.
Japanese Office Action for Application No. 2017-531921, dated Oct. 15, 2019 with Translation.

*Primary Examiner* — Aradhana Sasan
(74) *Attorney, Agent, or Firm* — The Marbury Law Group, PLLC

(57) ABSTRACT

The present invention relates to a composite particle comprising: at least one hydrophilic core particle; and a plurality of hydrophobic particles, wherein the surface of the hydrophilic core particle is substantially discontinuously covered by the hydrophobic particles. The novel composite particle according to the present invention can have surface active properties sufficient to prepare stable Pickering emulsions, and can maintain the surface active properties over a long period of time. The present invention also relates to a method for preparing the above composite particle.

17 Claims, No Drawings

(56) References Cited

FOREIGN PATENT DOCUMENTS

| | | |
|---|---|---|
| WO | 01/30144 A1 | 5/2001 |
| WO | 0130144 A1 | 5/2001 |
| WO | 02/43701 A2 | 6/2002 |
| WO | 2008/003685 A1 | 1/2008 |
| WO | 2008003685 A1 | 1/2008 |
| WO | 2009/013500 A1 | 1/2009 |
| WO | 2009013500 A1 | 1/2009 |
| WO | 2013/092158 A2 | 6/2013 |
| WO | 2013092158 A2 | 6/2013 |
| WO | 2014/010101 A1 | 1/2014 |
| WO | 2014/130763 A1 | 8/2014 |
| WO | 2014130763 A1 | 8/2014 |
| WO | 2014/186336 A1 | 11/2014 |
| WO | 2014186336 A1 | 11/2014 |

\* cited by examiner

COMPOSITE PARTICLE AND PREPARATION THEREOF

CROSS REFERENCE TO RELATED APPLICATIONS

This is a national stage application of PCT/JP2015/086148, filed internationally on Dec. 17, 2015, which claims priority to Japanese Application No. 2014-254742, filed on Dec. 17, 2014, both of which are incorporated by reference herein in their entireties.

TECHNICAL FIELD

The present invention relates to a composite particle based on a combination of a hydrophilic core particle and hydrophobic shell particles, and a method for preparing the composite particle.

BACKGROUND ART

Many types of composite particles such as amphiphilic particles are used especially in the field of cosmetics. Amphiphilic particles tend to aggregate at the interface between oil and water. Recently, several types of amphiphilic particles (surface active particles) are used for the stabilization of oil/water interfaces. As the amphiphilic particles, for example, surface-treated inorganic or organic particles are used. Emulsions with the oil/water interface stabilized by amphiphilic particles are called "Pickering emulsions".

In general, the above amphiphilic (surface active) particles have been prepared by surface modification techniques such as surface treatments by the adsorption of molecules on the surface of particles. For example, small surfactant molecules or polymer chains are adsorbed onto the surface of particles in many cases.

However, there are the following problems in surface treatment via adsorption.

- The adsorbed molecules tend to detach from the surface of amphiphilic particles. For example, depending on the environmental conditions around the particles, the adsorbed molecules are prone to detach, and therefore, the amphiphilic properties of the particles can easily be lost over a long period of time.
- It is difficult to control the degree of surface modification due to the use of small molecules.
- It is also difficult to measure the degree of surface modification without special equipment.
- The process to prepare amphiphilic particles is intricate and not easy to carry out. For example, a purification step to remove unadsorbed molecules is necessary. In addition, in some cases, pulverizing or grinding may be necessary to prepare the amphiphilic particles (for example, JP-A-2011-83753). However, it is difficult to precisely control the amphiphilic properties of the particles by adjusting the step of pulverizing or grinding.

On the other hand, as a type of surface modification technique, it has been known to covalently bond small molecules to the surface of particles. For example, hydrophilic silica particles may be treated with a silane coupling agent to form a hydrophobic film (derived from the silane coupling agent) which is covalently bonded to the surface of the silica particles. The surface of the treated silica particles may become hydrophobic. The covalently bonded film is not easily detached (cf. Hyomen, Vol. 41, No. 6, p.28-34 (2003)).

According to the above surface treatment using reagents to form a covalent bonding, the surface of the particles may be controlled to be somewhere between hydrophilic and hydrophobic by, for example, the type of reagents to be reacted with the particles. However, this control is not easy, and therefore, the surface active properties of the particles may be insufficient to prepare stable Pickering emulsions. Furthermore, it is necessary to remove unreacted reagents by a purification step. In addition, the reagents are in many cases harmful to human beings. Also, it is difficult to directly measure the degree of surface modification because the surface of the particles is treated with reagents having small molecules.

DISCLOSURE OF INVENTION

Thus, an objective of the present invention is to provide a novel composite particle which can have surface active properties sufficient to prepare stable Pickering emulsions, and can maintain the surface active properties over a long period of time.

The above objective of the present invention can be achieved by a composite particle comprising: at least one hydrophilic core particle; and a plurality of hydrophobic particles, wherein the surface of the hydrophilic core particle is substantially discontinuously covered by the hydrophobic particles.

According to a preferred embodiment of the invention, the composite particle comprises one hydrophilic core particle and two different types of hydrophobic particles, wherein the surface of the hydrophilic core particle is substantially discontinuously covered by the hydrophobic particles, preferably discontinuously covered by the hydrophobic particles.

It is preferable that the hydrophilic core particle and hydrophobic particles have a polarity difference characterized by $\Delta E = E_T(30)$ core hydrophilic particles $- E_T(30)$ hydrophobic shell particles superior to 2, preferably superior to 5.

The hydrophilic core particle may comprise at least one polysaccharide. Preferably, the hydrophilic core particle is constituted by or consists of at least one polysaccharide.

The weight ratio of the hydrophilic core particle(s) to the hydrophobic particles may be 70:30 to 80:20, preferably 80:20 to 90:10, and more preferably 90:10 to 99.9:0.1.

In another preferred embodiment, the weight ratio of the hydrophilic core particle(s) to the hydrophobic particles may be 10:90 to 70:30, preferably 15:85 to 50:50, even more preferably 20:80 to 30:70.

The mean particle size of the hydrophilic core particle may be from 100 nm to 200 μm, preferably from 500 nm to 50 μm, more preferably from 1 to 50 μm, even more preferably from 1 to 20 μm, and in particular from 1 to 10 μm.

90 vol % or more of the hydrophilic core particles may have a mean primary particle size ranging from 2 to 7 μm, preferably from 2 to 6 μm, and more preferably from 2 to 5 μm.

The ratio of the longest diameter/the shortest diameter of the hydrophilic core particle may range from 1.0 to 2.5, preferably from 1.0 to 2.0, and more preferably from 1.0 to 1.5.

The ratio of the wet point for water/the wet point for oil may be 5 or less, preferably 4 or less, and more preferably 2 or less.

The hydrophilic core particle may comprise at least one cellulose, preferably porous cellulose, and more preferably type II cellulose. Preferably, the hydrophilic core particle consists of cellulose.

The mean particle size of the hydrophobic particle may be from 10 nm to 100 µm, preferably from 10 nm to 20 µm, more preferably from 50 nm to 10 µm, and even more preferably from 0.1 to 1 µm.

The hydrophobic particle may comprise at least one selected from poly(meth)acrylates, polyalkyl(meth)acrylates, and styrene/acrylate copolymers such as cross-linked styrene/acrylate copolymers, preferably polyalkyl(meth)acrylates and cross-linked styrene/acrylate copolymers, and more preferably polymethyl(meth)acrylates and cross-linked styrene/methyl(meth)acrylate copolymers. In a preferred embodiment, the hydrophobic particle consists of polymethyl(meth)acrylates. In another preferred embodiment, the hydrophobic particle consists of cross-linked styrene/methyl methacrylate.

From 10 to 90%, preferably 10 to 70%, and more preferably 30 to 50% of the surface of the hydrophilic core particle may be covered by the hydrophobic particles.

Another objective of the present invention is to provide a novel method which can easily and safely prepare the above novel composite particle without any purification process, and can easily and precisely control the surface active properties of the composite particle.

The above objective of the present invention can be achieved by a method for preparing the composite particle, comprising a step of subjecting: at least one hydrophilic core particle; and a plurality of hydrophobic particles to a mechanochemical fusion process, preferably a hybridizer process, wherein the weight ratio of the hydrophilic core particle(s) to the hydrophobic particles is preferably 70:30 to 80:20, more preferably 80:20 to 90:10, and even more preferably 90:10 to 99.9:0.1.

In one particular embodiment of the present invention, the composite particle may be prepared by a method comprising a step of subjecting at least one hydrophilic core particle; and a plurality of hydrophobic particles to a mechanochemical fusion process, preferably a hybridizer process, wherein the weight ratio of the hydrophilic core particle(s) to the hydrophobic particles is preferably 10:90 to 70:30, preferably 15:85 to 50:50, even more preferably 20:80 to 30:70.

Preferably, the composite particle may be prepared by subjecting one hydrophilic core particle and two different types of hydrophobic particles to a mechanochemical fusion process, wherein the weight ratio of the hydrophilic core particle to the hydrophobic particles is preferably 10:90 to 70:30, preferably 15:85 to 50:50, even more preferably 20:80 to 30:70.

The present invention also relates to a composition comprising at least one composite particle according to the present invention.

In particular, the present invention also relates to a composition comprising, in a physiologically acceptable medium, at least one composite particle according to the present invention.

The present invention also relates to a non-therapeutic cosmetic process comprising the application, to the surface of the keratin material, of at least one composition according to the present invention.

In particular, the present invention also relates to a non-therapeutic cosmetic process for caring for and/or making up a keratin material, comprising the application, to the surface of the keratin material, of at least one composition according to the present invention.

BEST MODE FOR CARRYING OUT THE INVENTION

After diligent research, the inventors have discovered that it is possible to prepare a new composite particle which can have surface active properties sufficient to prepare stable Pickering emulsions, and can maintain the surface active properties over a long period of time, by a new method which can easily and safely prepare the composite particle without any purification process, and can easily and precisely control the surface active properties of the composite particle.

The new composite particle according to the present invention comprises a composite particle comprising: at least one hydrophilic core particle; and a plurality of hydrophobic particles, wherein the surface of the hydrophilic core particle is substantially discontinuously covered by the hydrophobic particles, preferably discontinuously covered by the hydrophobic particles.

In a particular embodiment of the present invention, the new composite particle comprises: at least one hydrophilic core particle; and two types of hydrophobic particles, wherein the surface of the hydrophilic core particle is substantially discontinuously covered by the hydrophobic particles, preferably discontinuously covered by the hydrophobic particles. The term "substantially discontinuously covered" means at least 0.1%, preferably at least 10%, more preferably at least 50%, even more preferably at least 70%, most preferably at least 90%, in particular at least 95% of the surface of the hydrophilic core particle is not covered by the hydrophobic particles.

The new method for preparing the composite particle according to the present invention comprises a step of subjecting: at least one hydrophilic core particle; and a plurality of hydrophobic particles to a mechanochemical fusion process, preferably a hybridizer process. Preferably, the weight ratio of the hydrophilic core particle(s) to the hydrophobic particles is 70:30 to 80:20, more preferably 80:20 to 90:10, and even more preferably 90:10 to 99.9:0.1.

In a preferred embodiment, the new method for preparing the composite particle according to the present invention comprises a step of subjecting: at least one hydrophilic core particle; and two types of hydrophobic particles to a mechanochemical fusion process, preferably a hybridizer process. Preferably, the weight ratio of the hydrophilic core particle(s) to the hydrophobic particles is 70:30 to 80:20, more preferably 80:20 to 90:10, and even more preferably 90:10 to 99.9:0.1.

In another preferred embodiment, the weight ratio of the hydrophilic core particle(s) to the two hydrophobic particles may be 10:90 to 70:30, preferably 15:85 to 50:50, even more preferably 20:80 to 30:70.

According to the present invention, the hydrophobic particles strongly attach to the surface of the hydrophilic core particle, and therefore, it is difficult for the hydrophobic particles to detach from the hydrophilic core particle. The hydrophobic particles can be maintained in an attached state on the hydrophilic core particle, and therefore, the composite particle according to the present invention can be amphiphilic, and can have surface active properties over a long period of time.

For the purpose of the invention, the term "amphiphilic composite particles" means that the said composite particles have a hydrophilic portion and a hydrophobic portion, wherein the said hydrophilic portion and hydrophobic portion have different polarities which allow them to assemble at the interface between oil and water of a composition containing oil and water.

The polarity of the hydrophilic particles and hydrophobic particles of the composite particles of the invention may be determined with the scale $E_T(30)$, by measuring the solvachromic effect of a dye as the compound 4-(2,4,6-triphenylpyridinium)-2,6-diphenylphenoxide (Reichardt's dye) in contact with the material. This method is disclosed in the publication of Dimroth et coll., [Justus Liebigs Annalen der Chemie, 661 (1), 1-37, (1963)] for this principle. The ET(30) values were defined for different materials by Spange et coll., [Langmuir, 15 (6), 2103-2111, (1999)], [J. Phys. Chem. B, 104 (27), 6417-6428, (2000)], ["Natural Fibre Reinforced Polymer Composites from Macro to Nanoscales", Old City Publishing, First Edition 2009, pages 47-72] and [Macromol. Rapid Commun. 21, 643-659 (2000)].

The parameter $E_T(30)$ (expressed in kcal.mol−1) is from 30.7 for the Tetramethylsilane to 63.1 for water.

If we consider ΔE as the polarity difference, according to the scale $E_T(30)$, between hydrophilic core particles and hydrophobic shell particles, it will be determined by the following equation:

$$\Delta E = E_T(30) \text{ core hydrophilic particles} - E_T(30) \text{ hydrophobic shell particles}$$

Preferably, the hydrophilic core particles and hydrophobic particles will be selected such that ΔE is superior to 2, and more preferably superior to 5.

The composite particle according to the present invention can be used to prepare stable Pickering O/W emulsions due to the sufficient surface active properties provided by a combination of the hydrophilic core particle and the hydrophobic shell particles. The Pickering O/W emulsions prepared using the composite particle according to the present invention can be stable over time.

The degree of surface modification of the hydrophilic core particle can be checked easily by, for example, scanning electron microscopy.

According to the present invention, the above composite particle can be easily and safely prepared because the mechanochemical fusion process can be easily performed and does not require any reagents which may be harmful or any purification process. In addition, the method according to the present invention can easily and precisely control the amphiphilic properties of the composite particle by, for example, the amount of the hydrophobic particles.

Thus, the method according to the present invention is simple and can easily prepare a composite particle comprising: at least one hydrophilic core particle; and a plurality of hydrophobic particles, preferably two different types of hydrophobic particles, wherein the surface of the hydrophilic core particle is substantially discontinuously, preferably discontinuously covered by the hydrophobic particles, and the hydrophobic particles firmly fixed on the hydrophilic core particle, preferably via chemical and/or physical bonding other than covalent bonding. The composite particle can be amphiphilic, can have surface active properties over a long period of time, and can have surface active properties sufficient to prepare stable Pickering oil-in-water emulsions.

Hereafter, each of the elements constituting the composite particle and method according to the present invention will be described in a detailed manner.

[Hydrophilic Core Particle]

The composite particle according to the present invention comprises at least one hydrophilic core particle. The type of core particle is not limited as long as it is hydrophilic. Thus, a single type of hydrophilic particle or a combination of different types of hydrophilic particles may be used. According to a preferred embodiment of the invention, the composite particle comprises one hydrophilic core particle.

For the purpose of the invention, the term "hydrophilic particles" means that all the said particles are individually dispersed in an aqueous phase in such manner that they do not form aggregates.

The diameter of the hydrophilic core particles is not limited but may have a mean particle size of 10 nm or more, preferably 50 nm or more, more preferably 100 nm or more, even more preferably 200 nm or more, further more preferably 500 nm or more, and even further more preferably 1000 nm or more. The mean particle size of the hydrophilic core particle may preferably be 1000 μm or less, more preferably 500 μm or less, even more preferably 200 μm or less, further more preferably 50 μm or less, and even further more preferably 10 μm or less. Thus, it is possible that the hydrophilic core particle may have a mean particle size of from 100 nm to 200 μm, preferably from 500 nm to 50 μm, more preferably 1 to 50 μm, more preferably 1 to 20 μm, more preferably from 1 to 10 μm, and even more preferably from 0.1 to 1 μm.

It is preferable that the ratio of the longest diameter/the shortest diameter of the hydrophilic core particle range from 1.0 to 2.5, preferably from 1.0 to 2.0, and more preferably from 1.0 to 1.5.

It is preferable that 90 vol % or more of the hydrophilic core particles have a mean primary particle size ranging from 2 to 7 μm, preferably from 2 to 6 μm, and more preferably from 2 to 5 μm. If 90 vol % or more of the core particles have a mean primary particle size ranging from 2 to 7 μm, optical effects due to the core particles may also be achieved.

The mean (primary) particle size can be measured by, for example, measuring a photograph image obtained by SEM and the like, using a particle size analyzer such as a laser diffraction particle size analyzer, and the like. It is preferable to use a particle size analyzer such as a laser diffraction particle size analyzer.

The hydrophilic core particle may be made from inorganic materials or organic materials or a mixture thereof.

For example, the hydrophilic inorganic core particle may be made from metal oxides, in particular, transition metal oxides, such as zirconium oxides, cerium oxides, iron oxides, and titanium dioxide; talc; natural or synthetic mica; alumina; aluminosilicate; silica (or silicon dioxides); hollow silica microspheres such as "Silica Beads SB 700®" and "Silica Beads SB 700®" from the company Maprecos, "Sunspheres H-33®" and "Sunspheres H-51®" from the company Asahi Glass; kaolin; silicates such as clays; calcium carbonates; magnesium carbonates; magnesium hydrogen carbonates; glass and glass microcapsules; and mixtures thereof.

For example, the hydrophilic organic core particle may be made from natural or semi-synthetic polymers such as starches and polysaccharides; and mixtures thereof.

As the hydrophilic core particle, hydrophobic particles the surface of which has been made hydrophilic by, for example, chemical treatments may be used. As the hydrophobic particles, mention may be made of those shown below as hydrophobic shell particles.

It is preferable that the hydrophilic core particle comprise at least one polysaccharide. It is more preferable that the hydrophilic core particle consist of at least one polysaccharide.

The polysaccharide may be selected from starches, cellulose and its derivatives, and mixtures thereof. Cellulose and its derivatives are preferable. In a preferred embodiment of the present invention, the polysaccharide may be cellulose.

The cellulose and its derivatives which can be used as a material or materials for the hydrophilic core particle in the composite particle according to the present invention may be porous or non-porous. However, it is preferable that the cellulose and its derivatives be porous.

The porosity of the cellulose and its derivatives may be characterized by a specific surface area of from 0.05 m$^2$/g to 1,500 m$^2$/g, more preferably from 0.1 m$^2$/g to 1,000 m$^2$/g, and even more preferably from 0.2 m$^2$/g to 500 m$^2$/g according to the BET method. In the present invention, the cellulose that may be used is not limited by the type of cellulose such as cellulose I, cellulose II, or the like. As the cellulose which can be used as a material for the core particle in the composite particle according to the present invention, type II cellulose is preferable.

It is preferable that the cellulose which can be used as a material for the hydrophilic core particle in the composite particle according to the present invention be in the form of a particle, in particular a spherical particle.

The cellulose particle, preferably a spherical cellulose particle, can be prepared, for example, as follows.
(1) A slurry of calcium carbonate, as an aggregation inhibitor, is added to an alkaline water-soluble anionic polymer aqueous solution, and stirred.
(2) Viscose and the aqueous solution obtained in (1) above are mixed to form a dispersion of viscose fine particles.
(3) The dispersion of viscose fine particles obtained in (2) above is heated to aggregate the viscose in the dispersion, and neutralized with acid, to form cellulose fine particles.
(4) The cellulose fine particles are separated from the mother liquid obtained in (3) above, and washed and dried, if necessary.

The viscose is a raw material of the cellulose. It is preferable to use viscose with a gamma value of 30 to 100% by mass and an alkaline concentration of 4 to 10% by mass. As the above water-soluble anionic polymer, mention may be made of polyacrylic acid sodium salt, polystyrene sulfonic acid sodium salt, and the like. The above calcium carbonate is used to prevent the aggregation of viscose fine particles in the dispersion and to make the particle size of the cellulose particles smaller. As the calcium carbonate slurry, mention may be made of Tama Pearl TP-221GS marketed by Okutama Kogyo Co., Ltd. in Japan.

The hydrophilic core particle may or may not be coated beforehand.

In a particular embodiment, the hydrophilic core particle may have a coating. The material of the coating of the hydrophilic core particle is not limited, as long as the material is hydrophilic. As an example of the material of the coating, mention may be made of a mono- or di-carboxylic acid or a salt thereof, an amino acid, an N-acylamino acid, and an amido compound. As the material of the coating, potassium succinate and lauroyl lysine may be preferable. In a particular embodiment, the hydrophilic core particle may have a coating comprising a metal oxide, preferably titanium dioxide.

In other words, the hydrophilic core particles may have been surface-treated. As examples of surface treatments, mention may be made of the following:
(a) N-acylated lysine treatments;
(b) Polyacrylic acid treatments;
(c) Metal soap treatments such as those with stearate salt or myristate salt;
(d) Acrylic resin treatments; and
(e) Metal oxide treatments.

It is possible to perform a plurality of the above surface treatments in combination.

According to one embodiment, a cellulose derivative may be chosen from cellulose esters and ethers.

It is pointed out that the term "cellulose ester" means, in the text hereinabove and hereinbelow, a polymer consisting of an α (1-4) sequence of partially or totally esterified anhydroglucose rings, the esterification being obtained by reaction of all or only some of the free hydroxyl functions of the said anhydroglucose rings with a linear or branched carboxylic acid or carboxylic acid derivative (acid chloride or acid anhydride) containing from 1 to 4 carbon atoms.

Preferably, the cellulose ester results from the reaction of some of the free hydroxyl functions of the said rings with a carboxylic acid containing from 1 to 4 carbon atoms.

Advantageously, the cellulose esters are chosen from cellulose acetates, propionates, butyrates, isobutyrates, acetobutyrates and acetopropionates, and mixtures thereof.

These cellulose esters may have a weight-average molecular mass ranging from 3,000 to 1,000,000, preferably from 10,000 to 500,000 and more preferably from 15,000 to 300,000.

In the text hereinabove and hereinbelow, the term "cellulose ether" means a polymer consisting of an α (1-4) sequence of partially etherified anhydroglucose rings, some of the free hydroxyl functions of the said rings being substituted with a radical —OR, R preferably being a linear or branched alkyl radical containing from 1 to 4 carbon atoms.

The cellulose ethers are thus preferably chosen from cellulose alkyl ethers with an alkyl group containing from 1 to 4 carbon atoms, such as cellulose methyl, propyl, isopropyl, butyl and isobutyl ethers.

These cellulose ethers may have a weight-average molecular mass ranging from 3,000 to 1,000,000, preferably from 10,000 to 500,000 and more preferably from 15,000 to 300,000.

The polysaccharides for the hydrophilic core particle used for the composite particle according to the present invention may preferably have
a wet point for oil being at least 25 ml/100 g, preferably from 35 to 600 ml/100 g, and more preferably from 40 to 500 ml/100 g, and
a wet point for water being at least 50 ml/100 g, preferably from 100 to 600 ml/100 g and even more preferably from 150 to 500 ml/100 g.

The term "wet point for oil" in the specification means a quantity or amount of oil which is necessary to make the target powder completely wet, which can be recognized, in particular, by the formation of a paste with the target powder.

The wet point for oil can be determined by the following protocol.
(1) 2 g of a target powder is kneaded with a spatula on a glass plate while adding oil, in particular linear ester oil, such as isononyl isononanoate with a viscosity of 9 cP and a density of 0.853 g/ml.
(2) When the target powder becomes completely wet and starts to form a paste, the weight of the added oil is determined as the weight of the wet point.
(3) The wet point for oil is calculated from the equation: Wet point for oil (ml/100 g)={(the weight of wet point)/2 g}×100/the density of oil.

Similarly, the term "wet point for water" in the specification means a quantity or amount of water which is necessary to make the target powder completely wet, which can be recognized, in particular, by the formation of a paste with the target powder.

The wet point for water can be determined by the following protocol.
(1) 2 g of a target powder is kneaded with a spatula on a glass plate while adding water with a density of 0.998 g/ml.
(2) When the target powder becomes completely wet and starts to form a paste, the weight of the added water is determined as the weight of the wet point.
(3) The wet point for water is calculated from the equation: Wet point for water (ml/100 g)={(the weight of wet point)/2 g}×100/the density of water.

It is preferable that the ratio of the wet point for water/the wet point for oil of the hydrophilic core particle in the composite particle according to the present invention be 5 or less, preferably 4 or less, more preferably 3 or less, and even more preferably 2 or less.

As the hydrophilic core particle in the composite particle according to the present invention, mention may be made of, for example, the following spherical cellulose particles marketed by Daito Kasei in Japan:
Cellulobeads USF (wet point for oil is 296.0 ml/100 g, wet point for water is 400.8 ml/100 g, the ratio of the wet point for water/the wet point for oil is 1.4) with a particle size of 4 μm (porous cellulose),
Cellulobeads D-5 (wet point for oil is 49.8 ml/100 g, wet point for water is 205.0 ml/100 g, the ratio of the wet point for water/the wet point for oil is 4.1) with a particle size of 10 μm;
Cellulobeads D-10 (wet point for oil is 44.0 ml/100 g, wet point for water is 164.0 ml/100 g, the ratio of the wet point for water/the wet point for oil is 3.7) with a particle size of 15 μm;
MOISCELL PW D-5 XP (wet point for oil is 58.6 ml/100 g, wet point for water is 281.5 ml/100 g, the ratio of the wet point for water/the wet point for oil is 4.8) with a particle size of 10 μm (potassium succinate cellulose); and
MOISCELL PW D-50 XP (wet point for oil is 39.9 ml/100 g, wet point for water is 160.0 ml/100 g, the ratio of the wet point for water/the wet point for oil is 4) with a particle size of 50 μm (potassium succinate cellulose).

Cellulobeads USF and Cellulobeads D-5 are preferable. Cellulobeads USF are most preferable.

[Hydrophobic Particles]

The surface of the hydrophilic core particle in the composite particle according to the present invention is substantially discontinuously, preferably discontinuously covered by hydrophobic particles. In other words, not all or all the surface of the hydrophilic core particle is covered or coated by hydrophobic particles. The hydrophobic particles may be referred to as shell particles around the core particle.

It may be preferable that from 10 to 90%, preferably 10 to 70%, and more preferably 30 to 50% of the surface of the hydrophilic core particle is covered by the hydrophobic particles.

Since hydrophobic shell particles are present on the surface of the hydrophilic core particle and an uncovered hydrophilic surface of the hydrophilic core particle is present, the composite particle according to the present invention can be amphiphilic, and can have surface active effects.

The type of the shell particle is not limited as long as it is hydrophobic. Thus, a single type of hydrophobic particle or a combination of different types of hydrophobic particles may be used. According to a preferred embodiment of the invention, the composite particle comprises hydrophilic core particles, preferably one core particle, and at least two different types of hydrophobic particles, preferably two different types of hydrophobic particles.

For the purpose of the invention, the term "hydrophobic particles" means that all the said particles are individually dispersed in an oily phase in such manner that they do not form aggregates.

The diameter of the hydrophobic shell particles is not limited but may have a mean particle size of 10 nm or more, preferably 50 nm or more, and more preferably 100 nm or more. The mean particle size of the hydrophobic shell particle may preferably be 100 μm or less, more preferably 50 μm or less, even more preferably 20 μm or less, further more preferably 5 μm or less, and even further more preferably 1 μm or less. Thus, it is possible that the hydrophobic shell particle may have a mean particle size of from 10 nm to 100 μm, preferably from 10 nm to 20 μm, more preferably from 50 nm to 10 μm, and even more preferably from 0.1 to 1 μm.

In one particular embodiment of the present invention, the composite particle comprises at least one hydrophilic core particle and at least two hydrophobic particles that have different mean particles sizes. Preferably, the composite particle comprises one hydrophilic core particle and two different types of hydrophobic particles characterized by a ratio of their mean particles sizes of 1:2 to 1:10000, preferably 1:10 to 1:1500. More preferably, one hydrophobic shell particle may have a mean particle size of from 50 nm to 1 μm and the other hydrophobic shell particle may have a mean particle size of from 1 μm to 50 μm.

It is preferable that the ratio of the longest diameter/the shortest diameter of the hydrophobic shell particle range from 1.0 to 2.5, preferably from 1.0 to 2.0, and more preferably from 1.0 to 1.5.

The mean (primary) particle size can be measured by, for example, measuring a photograph image obtained by SEM and the like, using a particle size analyzer such as a laser diffraction particle size analyzer, and the like. It is preferable to use a particle size analyzer such as a laser diffraction particle size analyzer.

The hydrophobic shell particles may be colorless or white powder. For example, the hydrophobic shell particles may be selected from fillers and/or optical materials which are conventionally used in cosmetics.

The hydrophobic shell particles may be hollow or not or a mixture thereof.

The hydrophobic shell particle may be made from inorganic materials or organic materials or a mixture thereof.

For example, the hydrophobic organic shell particle may be made from synthetic polymers such as polyamides (Nylon®), poly-β-alanine and polyethylene powders; tetrafluoroethylene polymer (Teflon®) powders; silicone resin microbeads, for instance "Tospearls®" from the company Toshiba; acrylate polymer microspheres such as those made from crosslinked acrylate copolymer "Polytrap 6603®" from the company R.P. Scherrer and those made from polymethylmethacrylate "Micropearl M100®" from the company SEPPIC; polyurea powders; polyurethane powders such as the hexamethylene diisocyanate and trimethylol hexyl lactone copolymer powder sold under the name "Plastic Powder D-400®" by the company Toshiki;

microcapsules of methyl acrylate or methacrylate polymers or copolymers, or alternatively, vinylidene chloride and acrylonitrile copolymers, for instance, "Expancel®" from the company Expancel; elastomeric crosslinked organopolysiloxane powders such as those sold under the name "KSP100®" by the company Shinetsu Chemical; and mixtures thereof.

It is preferable that the hydrophobic shell particle comprise at least one selected from poly(meth)acrylates, polyalkyl(meth)acrylates, and styrene/acrylates copolymers, preferably polyalkyl(meth)acrylates and cross-linked styrene/acrylate copolymers, and more preferably polymethyl (meth)acrylates and cross-linked styrene/methyl methacrylate copolymers. It is more preferable that the hydrophobic shell particle consist of at least one selected from poly(meth) acrylates and polyalkyl(meth)acrylates, cross-linked styrene/acrylates copolymers even more preferably polyalkyl (meth)acrylates, and even further more preferably polymethyl(meth)acrylates or cross-linked styrene/methyl methacrylate. In a preferred embodiment, the hydrophobic shell particle consists of polymethyl(meth)acrylates. In another preferred embodiment, the hydrophobic shell particle consists of cross-linked styrene/methyl methacrylate.

As examples of the hydrophobic shell particles, mention may be made of:
Polymethylmethacrylates such as MP-2200 marketed by Soken in Japan, Cross-linked polymethylmethacrylate porous particles such as PAC-M810 and cross-linked styrene/acrylate copolymer hollow-core particles such as SUN-SPHERES marketed by Dow.

As the hydrophobic shell particles, polymethylmethacrylates such as MP-2200 marketed by Soken in Japan and cross-linked styrene/acrylate copolymer hollow-core particles SUNSPHERES marketed by Doware in particular preferable.

It is preferable that the weight ratio of the hydrophilic core particle(s) to the hydrophobic particles be 70:30 to 80:20, preferably 80:20 to 90:10, and more preferably 90:10 to 99.9:0.1.

In another preferred embodiment, the weight ratio of the hydrophilic core particle(s) to the hydrophobic particles may be 10:90 to 70:30, preferably 15:85 to 50:50, even more preferably 20:80 to 30:70.

(Particulate Inorganic UV Filter as Hydrophobic Shell Particle)

As the hydrophobic shell particles, a particulate inorganic UV filter may be used. If two or more particulate inorganic UV filters are used, they may be the same or different, preferably the same. The term "UV filters" may be rephrased as "UV screening agents".

Inorganic UV filters may be used as the hydrophobic shell particles as long as the surface of the inorganic UV filters is hydrophobic or modified as hydrophobic. If two or more inorganic UV filters are used, they may be the same or different, preferably the same.

The inorganic UV filter used for the present invention may be active in the UV-A and/or UV-B region, preferably in the UV-B region or in the UV-A and UV-B region. It is preferable that the active UV filtering region of the inorganic UV filter and that of the particulate organic UV filter be complementary to each other, in order to provide comprehensive UV protection. For example, it is preferable that the inorganic UV filter be active at least in the UV-B region and the particulate organic UV filter be active at least in the UV-A region. The inorganic UV filter may be hydrophilic and/or lipophilic. The inorganic UV filter is completely insoluble in solvents such as water and ethanol commonly used in cosmetics.

The inorganic UV filter can be coated by an organic UV filter and it is preferable that the active UV filtering region of the inorganic UV filter and that of the organic UV filter be complementary to each other, in order to provide comprehensive UV protection.

It is preferable that the inorganic UV filter be in the form of a fine particle such that the mean (primary) particle diameter thereof ranges from 1 nm to 50 nm, preferably 5 nm to 40 nm, and more preferably 10 nm to 30 nm. The mean (primary) particle size or mean (primary) particle diameter here is an arithmetic mean diameter.

The inorganic UV filter may be selected from the group consisting of silicon carbide, metal oxides which have been coated, and mixtures thereof.

Preferably, the inorganic UV filters are selected from pigments (mean size of the primary particles: generally from 5 nm to 50 nm, preferably from 10 nm to 50 nm) formed of metal oxides, such as, for example, pigments formed of titanium oxide (amorphous or crystalline in the rutile and/or anatase form), iron oxide, zinc oxide, zirconium oxide or cerium oxide, which are all UV photoprotective agents well known per se. Preferably, the inorganic UV filters are selected from titanium oxide, zinc oxide, and more preferably titanium oxide.

The surface of the inorganic UV filter should be modified to be hydrophobic, if the inorganic UV filter is hydrophilic. The inorganic UV filter may have at least one hydrophobic coating. The coating may comprise at least one compound selected from the group consisting of silicones, silanes, fatty acids or salts thereof (such as sodium, potassium, zinc, iron or aluminum salts), fatty alcohols, waxes such as beeswax, (meth)acrylate polymers, and (per)fluoro compounds.

If the coating includes silicones, the silicones in the coating(s) may be organosilicon polymers or oligomers comprising a linear or cyclic and branched or cross-linked structure, of variable molecular weight, obtained by polymerization and/or polycondensation of suitable functional silanes and essentially composed of a repetition of main units in which the silicon atoms are connected to one another via oxygen atoms (siloxane bond), optionally substituted hydrocarbon radicals being connected directly to the said silicon atoms via a carbon atom.

The term "silicones" also encompasses silanes necessary for their preparation, in particular alkylsilanes.

The silicones used for the coating(s) can preferably be selected from the group consisting of alkylsilanes, polydialkylsiloxanes and polyalkylhydrosiloxanes. More preferably still, the silicones are selected from the group consisting of octyltrimethylsilane, polydimethylsiloxanes and polymethylhydrosiloxanes.

Of course, the inorganic UV filters made of metal oxides may, before their treatment with silicones, have been treated with other surfacing agents, in particular with cerium oxide, alumina, silica, aluminum compounds, silicon compounds or their mixtures.

The coated inorganic UV filter may have been prepared by subjecting the inorganic UV filter to one or more surface treatments of a chemical, electronic, mechanochemical and/or mechanical nature with any of the compounds as described above.

The coated inorganic UV filters may be titanium oxide pigments with a coating on the surface thereof.

Titanium oxide pigments treated with a silicone are preferably $TiO_2$ treated with octyltrimethylsilane and for which the mean size of the individual particles is from 25 and 40 nm, such as that marketed under the trademark "T 805" by Degussa Silices, $TiO_2$ treated with a polydimethylsiloxane and for which the mean size of the individual particles is 21 nm, such as that marketed under the trademark "70250

Cardre UF TiO$_2$Si$_3$" by Cardre, anatase/rutile TiO$_2$ treated with a polydimethylhydrosiloxane and for which the mean size of the individual particles is 25 nm, such as that marketed under the trademark "Microtitanium Dioxide USP Grade Hydrophobic" by Color Techniques.

Preferably, the following coated TiO$_2$ can be used as the coated inorganic UV filter:
Stearic acid (and) Aluminum Hydroxide (and) TiO$_2$, such as the products "MT-100 TV" and/or "MT-10EX" from Tayca, with a mean primary particle diameter of 15 nm and 10 nm respectively;
Dimethicone (and) Stearic Acid (and) Aluminum Hydroxide (and) TiO$_2$, such as the product "SA-TTO-S4" from Miyoshi Kasei, with a mean primary particle diameter of 15 nm;
Silica (and) TiO$_2$, such as the product "MT-100 WP" from Tayca, with a mean primary particle diameter of 15 nm;
Dimethicone (and) Silica (and) Aluminum Hydroxide (and) TiO$_2$, such as the products "MT-Y02" and "MT-Y-110 M3 S" from Tayca, with a mean primary particle diameter of 10 nm;
Dimethicone (and) Aluminum Hydroxide (and) TiO$_2$, such as the product "SA-TTO-S3" from Miyoshi Kasei, with a mean primary particle diameter of 15 nm;
Dimethicone (and) Alumina (and) TiO$_2$, such as the product "UV TITAN M170" from Sachtleben, with a mean primary particle diameter of 15 nm; and
Silica (and) Aluminum Hydroxide (and) Alginic Acid (and) TiO$_2$, such as the product "MT-100 AQ" from Tayca, with a mean primary particle diameter of 15 nm.

In terms of UV filtering ability, TiO$_2$ coated with at least one organic UV filter is more preferable. For example, Avobenzone (and) Stearic Acid (and) Aluminum Hydroxide (and) TiO$_2$, such as the product "HXMT-100ZA" from Tayca, with a mean primary particle diameter of 15 nm, can be used.

The coated zinc oxide pigments are, for example:
those marketed under the trademark "Oxide Zinc CS-5" by Toshiba (ZnO coated with polymethylhydrosiloxane);
those marketed under the trademark "Nanogard Zinc Oxide FN" by Nanophase Technologies (as a 40% dispersion in Finsolv TN, C$_{12}$-C$_{15}$ alkyl benzoate);
those marketed under the trademark "Daitopersion Zn-30" and "Daitopersion Zn-50" by Daito (dispersions in oxyethylenated polydimethylsiloxane/cyclopolymethylsiloxane comprising 30% or 50% of zinc nano-oxides coated with silica and polymethylhydrosiloxane);
those marketed under the trademark "NFD Ultrafine ZnO" by Daikin (ZnO coated with phosphate of perfluoroalkyl and a copolymer based on perfluoroalkylethyl as a dispersion in cyclopentasiloxane);
those marketed under the trademark "SPD-Z1" by Shin-Etsu (ZnO coated with a silicone-grafted acrylic polymer dispersed in cyclodimethylsiloxane);
those marketed under the trademark "Escalol Z100" by ISP (alumina-treated ZnO dispersed in an ethylhexyl methoxycinnamate/PVP-hexadecene copolymer/methicone mixture); and
those marketed under the trademark "Fuji ZnO-SMS-10" by Fuji Pigment (ZnO coated with silica and polymethylsilsesquioxane); those marketed under the trademark "Nanox Gel TN" by Elementis (ZnO dispersed at 55% in C$_{12}$-C$_{15}$ alkyl benzoate with hydroxystearic acid polycondensate).

The coated iron oxide pigments are, for example, marketed by Arnaud under the trademarks "Nanogard WCD 2008 (FE 45B FN)", "Nanogard WCD 2009 (FE 45B 556)", "Nanogard FE 45 BL 345" and "Nanogard FE 45 BL" or by BASF under the trademark "Oxyde de fer transparent".

If the composite particle according to the present invention has hydrophobic shell particles of inorganic UV filters, the composite particle can have not only surface active effects but also UV shielding effects. Furthermore, the composite particle can have an effect of imparting a transparent or clear appearance, because the fine particles of the particulate inorganic UV filter(s) do not aggregate but spread on the core particle.

In one preferred embodiment according to the invention, the composite particle comprises one hydrophilic core particle and a first hydrophobic shell particle comprising at least one organic material and particulate inorganic UV filter as a second hydrophobic shell particle. Preferably, the composite particle comprises one hydrophilic core particle consisting of a polysaccharide or a polysaccharide derivative and a first hydrophobic shell particle comprising at least one synthetic polymer material and particulate inorganic UV filter comprising titanium dioxide as a second hydrophobic shell particle. Even more preferably, the composite particle comprises one core particle consisting of cellulose and/or of a cellulose ester derivative and/or of a cellulose ether derivative and a first hydrophobic shell particle comprising cross-linked styrene/methacrylate copolymers and particulate inorganic UV filter comprising titanium dioxide as a second hydrophobic shell particle. In particular, the composite particle comprises one core particle consisting of cellulose and/or of a cellulose ester derivative and/or of a cellulose ether derivative and a first hydrophobic shell particle comprising cross-linked styrene/methacrylate copolymers and particulate inorganic UV filter consisting of titanium dioxide, coated with stearic acid aluminum hydroxide, as a second hydrophobic shell particle.

(Method for Preparing Composite Particle)

The composite particle according to the present invention can be prepared by subjecting at least one hydrophilic core particle; and
a plurality of hydrophobic particles, preferably two different types of hydrophobic particles to a mechanochemical fusion process,
wherein,
the weight ratio of the hydrophilic core particle(s) to the hydrophobic particles is preferably 70:30 to 80:20, more preferably 80:20 to 90:10, and even more particularly 90:10 to 99.9:0.1.

In another preferred embodiment, the weight ratio of the hydrophilic core particle(s) to the hydrophobic particles may be 10:90 to 70:30, preferably 15:85 to 50:50, even more preferably 20:80 to 30:70.

As the hydrophilic core particle, those explained above may be used As the hydrophobic particles, those explained above, as well as the particulate inorganic UV filters explained above, may be used.

Mechanochemical fusion process means a process in which mechanical power such as impact force, friction force or shear force is applied to a plurality of subjects to cause fusion between the subjects.

The mechanochemical fusion process may be performed by, for example, an apparatus comprising a rotating chamber and a fixed inner piece with a scraper, such as a mechanofusion system marketed by Hosokawa Micron Corporation in Japan. The mechanochemical fusion process may be performed as well, using an apparatus equipped with a high-speed rotor having a plurality of blades in a chamber in dry conditions, such as the mechanofusion process marketed by Hosokawa Micron Corporation in Japan.

It is preferable to use a hybridizer process as the mechanochemical fusion process.

The hybridizer process was developed in the 1980s. The hybridizer process is a class of mechanochemical fusion processes in which strong mechanical power is applied to a plurality of particles to cause a mechanochemical reaction to form a composite particle.

According to the hybridizer process, the mechanical power is imparted by a high-speed rotor which can have a diameter from 10 cm to 1 m, and can rotate at a speed of 1,000 rpm to 100,000 rpm. Therefore, the hybridizer process can be defined as a mechanochemical fusion process using such a high-speed rotor. The hybridizer process is performed in air or under dry conditions. Thus, due to the high-speed rotation of the rotor, high-speed air flow may be generated near the rotor. However, some liquid materials may be subjected to the hybridizer process together with solid materials. The term "hybridizer process" has been used as a technical term.

According to another embodiment of the present invention, the mechanical power may be imparted by a high-speed rotor that can rotate at a linear velocity of 10 to 1000 m/s, preferably 20 to 100 m/s.

The hybridizer process can be performed by using a hybridization system marketed, for example, by Nara Machinery in Japan, in which at least two types of particles, typically core particles and fine particles, are fed into a hybridizer equipped with a high-speed rotor having a plurality of blades in a chamber under dry conditions, and the particles are dispersed in the chamber and mechanical and thermal energy (e.g., compression, friction and shear stress) are imparted to the particles for a relatively short period of time such as 1 to 60 minutes, preferably 1 to 30 minutes, even more preferably 1 to 10 minutes, and in particular 1 to 5 minutes. As a result, one type of particles (e.g., shell particles) is embedded or fixed on the other type of particles (e.g., core particle) to form composite particles. It is preferable that the particles have been subjected to electrostatic treatment(s) such as shaking to form an "ordered mixture" in which one type of particles is spread to cover the other type of particles. The hybridizer process can also be performed by using a theta composer marketed by Tokuju Corporation in Japan.

The hybridizer process can also be performed by using a Composi Hybrid or a Mechano Hybrid marketed by Nippon Coke.

According to one embodiment of the present invention, for example, hydrophilic core particles and hydrophobic shell particles can be fed into such a hybridizer to form a composite particle. The hybridizer process can be performed by using a rotor rotating at about 8,000 rpm (100 m/sec) for about 3 minutes.

In another embodiment of the present invention, the mechanochemical fusion process can be performed by using a rotor rotating at about 32.5 m/sec for about 20 minutes.

The mechanochemical fusion process, in particular the hybridizer process, can provide a composite particle in which core particles are in part or substantially discontinuously covered by hydrophobic particles which include those explained above, and may optionally include at least one hydrophobic inorganic UV filter explained above.

In one preferred embodiment, the composite particle according to the present invention can be prepared by subjecting one hydrophilic core particle and a first hydrophobic shell particle comprising at least one organic material and particulate inorganic UV filter as a second hydrophobic shell particle. Preferably, the composite particle can be prepared by subjecting one hydrophilic core particle consisting of a polysaccharide or a polysaccharide derivative and a first hydrophobic shell particle comprising at least one synthetic polymer material and particulate inorganic UV filter comprising titanium dioxide as a second hydrophobic shell particle. Even more preferably, the composite particle can be prepared by subjecting one core particle consisting of cellulose and/or of a cellulose ester derivative and/or of a cellulose ether derivative and a first hydrophobic shell particle comprising cross-linked styrene/methacrylate copolymers and particulate inorganic UV filter comprising titanium dioxide as a second hydrophobic shell particle. In particular, the composite particle comprises one core particle consisting of cellulose and/or of a cellulose ester derivative and/or of a cellulose ether derivative and a first hydrophobic shell particle comprising cross-linked styrene/methacrylate copolymers and particulate inorganic UV filter consisting of titanium dioxide, coated with stearic acid aluminum hydroxide, as a second hydrophobic shell particle.

Furthermore, the mechanochemical fusion process, in particular the hybridizer process, can provide strong bonds or strong interactions between the surface of the hydrophilic core particle and the hydrophobic particles.

It is possible to add, if necessary, large particles which have a mean particle size larger than that of the core particles, in combination with the hydrophilic core particles.

If the large particle(s) are used in combination with the hydrophilic core particle(s), the hydrophobic shell particles can interact or be effectively bound on the surface of the hydrophilic core particle(s) due to the anchor effects by the collision of the large particle(s) against the hydrophilic core particle(s). Therefore, the surface active effects, and optionally UV filtering effects and/or optical effects, can be further enhanced.

It should be noted that the mechanochemical fusion process, in particular the hybridizer process, is quite different from other processes using, for example, a beads mill and a jet mill. In fact, a beads mill causes pulverization or aggregation of core particles, and a jet mill causes pulverization of core particles making it difficult to form a uniform coating of a core particle by fine particles.

[Composition]

The present invention relates to a composition comprising at least one composite particle according to the present invention as described above.

Preferably, the composition according to the present invention can comprise, in a physiologically acceptable medium, at least one composite particle according to the present invention as described above. It is preferable that the composition according to the present invention is a cosmetic composition.

The term "physiologically acceptable medium" is intended to denote a medium that is particularly suitable for applying a composition according to the present invention to keratin materials.

The physiologically acceptable medium is generally adapted to the nature of the support onto which the composition is to be applied, and also to the form in which the composition is to be packaged.

The composite particle according to the present invention can be present in the composition according to the present invention in an amount ranging from 0.01% to 99% by weight, preferably from 0.1% to 50% by weight, and more preferably from 1% to 30% by weight, even more preferably 1% to 10% by weight, relative to the total weight of the composition.

Preferably, the composite particle according to the present invention can be used in compositions to be applied to keratin substances such as skin, lips, hair, and nails, providing superior surface active effects, and optionally UV shielding effects and/or optical effects, because the composite particle can exhibit good surface active functions due to the co-existence of the hydrophobic particles and the hydrophilic exposed surface, and optionally enhanced UV filtering effects and/or transparent or clear appearance and/or good optical effects such as more transparent or matt effect, without the risk of affecting the keratin substances. Furthermore, the composite particle according to the present invention can be easily formulated into cosmetic compositions, and can stabilize the cosmetic compositions.

According to one preferred embodiment of the present invention, the composite particle can be used in compositions to be applied to the skin of the body, the face, the lips, the hands and the décolleté, providing superior surface active effects and UV shielding effects and/or optical effects, preferably providing superior surface active effects and UV shielding effects and optical effects.

In a particular embodiment, the composite particle can be used in compositions to be applied to the skin of the body, the face, the lips, the hands and the décolleté, providing superior surface active effects and UV shielding effects.

In another particular embodiment, the composite particle can be used in compositions to be applied to the skin of the face and/or the lips providing superior surface active effects and optical effects.

The composition according to the present invention may be in various forms, for example, suspensions, dispersions, solutions, gels, emulsions, such as oil-in-water (O/W), creams, foams, milks, sticks, lip balms, dispersions of vesicles, for instance, of ionic and/or nonionic lipids, two-phase and multi-phase lotions, sprays, powders, and pastes. The composition may include an aqueous phase or water.

(Aqueous Phase)

The composition according to the present invention may comprise an aqueous phase.

The aqueous phase comprises water. The water that is suitable for use in the present invention may be a floral water such as cornflower water and/or a mineral water such as Vittel water, Lucas water or La Roche Posay water and/or a spring water.

The aqueous phase may also comprise water-miscible organic solvents (at room temperature: 25° C.), for instance monoalcohols containing from 2 to 6 carbon atoms, such as ethanol or isopropanol; polyols especially containing from 2 to 20 carbon atoms, preferably containing from 2 to 10 carbon atoms and preferentially containing from 2 to 6 carbon atoms, such as glycerol, propylene glycol, butylene glycol, pentylene glycol, hexylene glycol, dipropylene glycol or diethylene glycol; glycol ethers (especially containing from 3 to 16 carbon atoms) such as mono-, di- or tripropylene glycol ($C_1$-$C_4$)alkyl ethers, mono-, di- or triethylene glycol ($C_1$-$C_4$)alkyl ethers, and mixtures thereof.

The aqueous phase may also comprise stabilizers, for example sodium chloride, magnesium dichloride or magnesium sulfate.

The aqueous phase may also comprise any water-soluble or water-dispersible compound that is compatible with an aqueous phase, such as gelling agents, film-forming polymers, thickeners or surfactants, and mixtures thereof.

In particular, the composition according to the present invention may comprise an aqueous phase in a content ranging from 1 to 80% by weight, especially from 5 to 50% and more particularly from 10 to 45% by weight relative to the total weight of the composition.

(Fatty Phase)

The composition according to the present invention may comprise at least one liquid and/or solid fatty phase.

According to one embodiment, the composition according to the present invention is in the form of an emulsion.

In particular, the composition according to the present invention may comprise at least one liquid fatty phase, especially at least one oil as mentioned below.

In another embodiment, the composition according to the present invention may comprise at least one solid fatty acid phase, especially at least one wax, such as a natural wax and a synthetic wax. Examples of the natural wax include a petroleum wax, a plant wax, and an animal wax. Examples of the petroleum wax include a paraffin wax, a microcrystalline wax, and a petrolatum. Examples of the plant wax include rice wax, carnauba wax, candelilla wax, ouricury wax, Japan wax, cocoa butter, cork fibre wax and sugarcane wax. Examples of the animal wax include lanolin wax, lanolin derivatives and beeswax. Examples of the synthetic wax include a synthetic hydrocarbon wax and a modified wax. Examples of the synthetic hydrocarbon wax include polyethylene wax, polypropylene wax, and Fischer-Tropsch wax. Examples of the modified wax include a paraffin wax derivative, a montan wax derivative, and a microcrystalline wax derivative.

The term "oil" is understood to mean a fatty substance which is liquid at ambient temperature (25° C.).

The composition according to the present invention may comprise a liquid fatty phase in a content ranging from 1 to 90%, preferably from 5 to 80%, in particular from 10 to 70% and more particularly from 20 to 50% by weight relative to the total weight of the composition.

The fatty phase that is suitable for preparing the compositions according to the present invention may comprise hydrocarbon-based oils, silicone oils, fluoro oils or non-fluoro oils, or mixtures thereof.

The oils may be volatile or non-volatile.

They may be of animal, plant, mineral or synthetic origin.

The term "non-volatile oil" means an oil that remains on the skin or the keratin fiber at room temperature (25° C.) and atmospheric pressure. More specifically, a non-volatile oil has an evaporation rate strictly less than 0.01 mg/cm$^2$/min.

To measure this evaporation rate, 15 g of oil or of oil mixture to be tested are placed in a crystallizing dish 7 cm in diameter, which is placed on a balance in a large chamber of about 0.3 m$^3$ that is temperature-regulated, at a temperature of 25° C., and hygrometry-regulated, at a relative humidity of 50%. The liquid is allowed to evaporate freely, without stirring it, while providing ventilation by means of a fan (Papst-Motoren, reference 8550 N, rotating at 2700 rpm) placed in a vertical position above the crystallizing dish containing said oil or said mixture, the blades being directed towards the crystallizing dish, 20 cm away from the bottom of the crystallizing dish. The mass of oil remaining in the crystallizing dish is measured at regular intervals. The evaporation rates are expressed in mg of oil evaporated per unit of area (cm$^2$) and per unit of time (minutes).

The term "volatile oil" means any non-aqueous medium that is capable of evaporating on contact with the skin or the lips in less than one hour, at room temperature (25° C.) and atmospheric pressure. The volatile oil is a cosmetic volatile oil, which is liquid at room temperature (25° C.). More specifically, a volatile oil has an evaporation rate of between 0.01 and 200 mg/cm$^2$/min, limits included.

For the purposes of the present invention, the term "silicone oil" means an oil comprising at least one silicon atom, and especially at least one Si—O group.

The term "fluoro oil" means an oil comprising at least one fluorine atom.

The term "hydrocarbon-based oil" means an oil mainly containing hydrogen and carbon atoms.

The oils may optionally comprise oxygen, nitrogen, sulfur and/or phosphorus atoms, for example in the form of hydroxyl or acid radicals.

(Volatile Oils)

The volatile oils may be chosen from hydrocarbon-based oils containing from 8 to 16 carbon atoms, and especially $C_8$-$C_{16}$ branched alkanes (also known as isoparaffins), for instance isododecane (also known as 2,2,4,4,6-pentamethylheptane), isodecane and isohexadecane, for instance the oils sold under the trade names Isopar® or Permethyl®.

Volatile oils that may also be used include volatile silicones, for instance volatile linear or cyclic silicone oils, especially those with a viscosity of less than or equal to 8 centistokes (cSt) ($8 \times 10^{-6}$ $m^2$/s), and especially containing from 2 to 10 silicon atoms and in particular from 2 to 7 silicon atoms, these silicones optionally comprising alkyl or alkoxy groups containing from 1 to 10 carbon atoms. As volatile silicone oils that may be used in the present invention, mention may be made especially of dimethicones with viscosities of 5 and 6 cSt, octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, and mixtures thereof.

According to one embodiment, the composition of the present invention may comprise from 1 to 80% by weight, or even from 5 to 70% by weight, or even from 10 to 60% by weight and especially from 15 to 50% by weight of volatile oil relative to the total weight of the composition.

(Non-Volatile Oils)

The non-volatile oils may be chosen especially from non-volatile hydrocarbon-based, fluoro and/or silicone oils.

Non-volatile hydrocarbon-based oils that may especially be mentioned include:
- hydrocarbon-based oils of animal origin, such as perhydrosqualene,
- hydrocarbon-based oils of plant origin, such as phytostearyl esters, such as phytostearyl oleate, phytostearyl isostearate and lauroyl/octyldodecyl/phytostearyl glutamate (Ajinomoto, Eldew PS203), triglycerides formed from fatty acid esters of glycerol, in particular in which the fatty acids may have chain lengths ranging from $C_4$ to $C_{36}$ and especially from $C_{18}$ to $C_{36}$, these oils possibly being linear or branched, and saturated or unsaturated; these oils may especially be heptanoic or octanoic triglycerides, shea oil, alfalfa oil, poppy oil, winter squash oil, millet oil, barley oil, quinoa oil, rye oil, candlenut oil, passionflower oil, shea butter, aloe vera oil, sweet almond oil, peach stone oil, groundnut oil, argan oil, avocado oil, baobab oil, borage oil, broccoli oil, calendula oil, camelina oil, canola oil, carrot oil, safflower oil, flax oil, rapeseed oil, cotton oil, coconut oil, marrow seed oil, wheatgerm oil, jojoba oil, lily oil, macadamia oil, corn oil, meadowfoam oil, St John's Wort oil, monoi oil, hazelnut oil, apricot kernel oil, walnut oil, olive oil, evening primrose oil, palm oil, blackcurrant pip oil, kiwi seed oil, grapeseed oil, pistachio oil, winter squash oil, pumpkin oil, musk rose oil, sesame oil, soybean oil, sunflower oil, castor oil and watermelon seed oil, and mixtures thereof, or alternatively caprylic/capric acid triglycerides, such as those sold by the company Stearineries Dubois or those sold under the names Miglyol 810®, 812® and 818® by the company Dynamit Nobel,
- linear or branched hydrocarbons of mineral or synthetic origin, such as liquid paraffins and derivatives thereof, petroleum jelly, polydecenes, polybutenes, hydrogenated polyisobutene such as Parleam, and squalane;
- synthetic ethers containing from 10 to 40 carbon atoms;
- synthetic esters, for instance the oils of formula $R_1COOR_2$, in which $R_1$ represents a linear or branched fatty acid residue containing from 1 to 40 carbon atoms and $R_2$ represents a hydrocarbon-based chain, which is especially branched, containing from 1 to 40 carbon atoms, on condition that the sum of the number of carbon atoms in the chains $R_1$ and $R_2$ is greater than or equal to 10. The esters may be chosen especially from fatty acid esters of alcohols, for instance cetostearyl octanoate, isopropyl alcohol esters, such as isopropyl myristate, isopropyl palmitate, ethyl palmitate, 2-ethylhexyl palmitate, isopropyl stearate, isopropyl isostearate, isostearyl isostearate, octyl stearate, hydroxylated esters, for instance isostearyl lactate, octyl hydroxystearate, diisopropyl adipate, heptanoates, and especially isostearyl heptanoate, alcohol or polyalcohol octanoates, decanoates or ricinoleates, for instance propylene glycol dioctanoate, cetyl octanoate, tridecyl octanoate, 2-ethylhexyl 4-diheptanoate, 2-ethylhexyl palmitate, alkyl benzoates, polyethylene glycol diheptanoate, propylene glycol 2-diethylhexanoate, and mixtures thereof, $C_{12}$-$C_{15}$ alcohol benzoates, hexyl laurate, neopentanoic acid esters, for instance isodecyl neopentanoate, isotridecyl neopentanoate, isostearyl neopentanoate, octyldodecyl neopentanoate, isononanoic acid esters, for instance isononyl isononanoate, isotridecyl isononanoate, octyl isononanoate, hydroxylated esters, for instance isostearyl lactate and diisostearyl malate,
- polyol esters and pentaerythritol esters, for instance dipentaerythrityl tetrahydroxystearate/tetraisostearate,
- esters of diol dimers and of diacid dimers, such as Lusplan DD-DA5® and Lusplan DD-DA7® sold by the company Nippon Fine Chemical and described in patent application US 2004-175 338,
- copolymers of polyols and of diacid dimers, and esters thereof, such as Hailuscent ISDA or the dilinoleic acid/butanediol copolymer,
- fatty alcohols that are liquid at room temperature (25° C.), with a branched and/or unsaturated carbon-based chain containing from 12 to 26 carbon atoms, for instance 2-octyldodecanol, isostearyl alcohol, oleyl alcohol, 2-hexyldecanol, 2-butyloctanol and 2-undecylpentadecanol;
- $C_{12}$-$C_{22}$ higher fatty acids, such as oleic acid, linoleic acid or linolenic acid, and mixtures thereof,
- dialkyl carbonates, the two alkyl chains possibly being identical or different, such as dicaprylyl carbonate sold under the name Cetiol CC® by Cognis,
- oils of high molar mass, in particular having a molar mass ranging from about 400 to about 10 000 g/mol, in particular from about 650 to about 10 000 g/mol, in particular from about 750 to about 7500 g/mol and more particularly ranging from about 1000 to about 5000 g/mol. As oils of high molar mass that may be used in the present invention, mention may especially be made of oils chosen from:
  - lipophilic polymers,
  - linear fatty acid esters with a total carbon number ranging from 35 to 70,
  - hydroxylated esters, aromatic esters,
$C_{24}$-$C_{28}$ branched fatty acid or fatty alcohol esters,
silicone oils,
oils of plant origin, and
mixtures thereof;
optionally partially hydrocarbon-based and/or silicone fluoro oils, for instance fluorosilicone oils, fluoropolyethers and fluorosilicones as described in document EP-A-847 752;
silicone oils, for instance linear or cyclic non-volatile polydimethylsiloxanes (PDMS); polydimethylsiloxanes comprising alkyl, alkoxy or phenyl groups, which are pendant or at the end of a silicone chain, these groups containing from 2 to 24 carbon atoms; phenyl silicones, for instance phenyl trimethicones, phenyl dimethicones, phenyl trimethylsiloxy diphenyl siloxanes, diphenyl dimethicones, diphenyl methyldiphenyl trisiloxanes and 2-phenylethyl trimethylsiloxy silicates, and
mixtures thereof.

According to one particular embodiment, the fatty phase of the composition according to the present invention can contain only volatile compounds.

(Additives)

The composition according to the present invention may also comprise any additive usually used in the field under consideration, chosen, for example, from solvents, gums, anionic, cationic, amphoteric or nonionic surfactants, silicone surfactants, resins, thickening agents, structuring agents such as waxes, dispersants, antioxidants, essential oils, preserving agents, fragrances, neutralizers, antiseptics, UV-screening agents, pigments, dyes, anti-ageing agents, cosmetic active agents, such as vitamins, moisturizers, emollients or collagen-protecting agents, and mixtures thereof.

It is a matter of routine operations for a person skilled in the art to adjust the nature and amount of the additives present in the composition in accordance with the present invention such that the desired cosmetic properties are not thereby affected.

The composition according to the present invention may be in the form of a so-called Pickering emulsion wherein the oil and water phase are stabilized by the composite particle according to the present invention. The Pickering emulsion is generally in the form of an O/W emulsion. The Pickering O/W emulsion can maintain the form of the emulsion without any conventional surfactant, and therefore, it can include no conventional liquid surfactant.

The composite particle according to the present invention has sufficient surface active effects, and therefore it can be used to prepare stable Pickering O/W emulsions. The Pickering O/W emulsions prepared by using the composite particle according to the present invention can be stable over time.

The composition according to the present invention may have additional cosmetic effects such as better UV filtering effects and better optical effects, if the hydrophobic particles comprise inorganic UV filter(s).

According to another embodiment, the composition according to the present invention may be in the form of a foam.

According to this embodiment, the composition according to the present invention can be packaged in a foam dispenser. It can involve either products referred to as "aerosols" dispensed from a pressurized container by means of a propellant gas and thus forming a foam at the time of their dispensing, or products dispensed from a container by means of a mechanical pump connected to a dispensing head where the passage of the composition through the dispensing head transforms it into a foam in the area of the outlet orifice of such a head at the latest.

According to a first variant, the dispenser can be an aerosol furthermore containing the composition according to the present invention; and a propellant gas. For the purposes of the present invention, the term "propellant" means any compound that is gaseous at a temperature of 20° C. and at atmospheric pressure, and that can be stored under pressure in liquid or gaseous form in an aerosol container. The propellant may be chosen from optionally halogenated volatile hydrocarbons, such as n-butane, propane, isobutane, pentane or a halogenated hydrocarbon, and mixtures thereof. Carbon dioxide, nitrous oxide, dimethyl ether (DME), nitrogen or compressed air may also be used as propellant. Mixtures of propellants may also be used. Dimethyl ether and/or non-halogenated volatile hydrocarbons are preferably used.

The propellant gas which can be used may be chosen among the previously mentioned gases and in particular among carbon dioxide, nitrogen, nitrogen oxide, dimethyl ether, volatile hydrocarbons such as butane, isobutane, propane and pentane, and mixtures thereof.

According to another variant, the composition according to the present invention can be in a "pump bottle" type foam dispenser. These dispensers include a dispensing head for delivering the composition, a pump and a plunger tube for transferring the composition from the container, into the head, for dispensing the product. The foam is formed by forcing the composition to pass through a material including a porous substance such as a sintered material, a filtering grid of plastic or metal, or similar structures.

Such dispensers are known to persons skilled in the art and are described in the patents: U.S. Pat. No. 3,709,437 (Wright), U.S. Pat. No. 3,937,364 (Wright), U.S. Pat. No. 4,022,351 (Wright), U.S. Pat. No. 4,147,306 (Bennett), U.S. Pat. No. 4,184,615 (Wright), U.S. Pat. No. 4,598,862 (Rice), U.S. Pat. No. 4,615,467 (Grogan et al.), and U.S. Pat. No. 5,364,031 (Tamiguchi et al.).

[Cosmetic Process]

The composition, in particular the cosmetic composition, according to the present invention can be used in a non-therapeutic cosmetic process for caring for and/or making up a keratin material, comprising the application, to the surface of the keratin material, of at least one composition according to the present invention.

The keratin substance here means a material containing keratin as a main constituent element, and examples thereof include skin, nails, lips, eyebrows, lashes, hair and the like.

For caring for the keratin material, the cosmetic composition according to the present invention may be used as a lotion, a cream, a hair tonic, a hair conditioner, a sun screening agent, and the like. For making up the keratin material, the cosmetic composition according to the present invention may be used as a foundation, a mascara, a lipstick, a lip gloss, a blusher, an eye shadow, a nail varnish, and the like.

It is to be understood that a person skilled in the art can choose the appropriate presentation form, as well as its method of preparation, on the basis of his/her general knowledge, taking into account the nature of the constituents used, for example, their solubility in the vehicle, and the application envisaged for the composition.

EXAMPLES

The present invention will be described in more detail by way of examples, which however should not be construed as limiting the scope of the present invention.

Examples 1-3

The components shown in Tables 1 and 2 were subjected to a hybridizer process using a Hybridizer equipped with a high-speed rotor having a plurality of blades in a chamber in dry conditions, marketed by Nara Machinery Co., Ltd. in Japan to obtain a composite particle according to Examples 1-3.

In detail, for each of Examples 1-3, the components shown in Tables 1 and 2 were mixed at the mixing ratio (the numerals in Table 1 and 2 are based on parts by weight) shown in Tables 1 and 2 in a plastic bag by shaking by hand for a short period of time. The mixture was put in the Hybridizer, and the rotor was rotated at 8,000 rpm (100 m/s linear velocity) for 3 minutes to obtain the composite particle according to each of Examples 1-3.

TABLE 1

|  | Core Particle Cellulose[1] | Shell Particle PMMA |
|---|---|---|
| Example 1 | 97.5 | 2.5 |

TABLE 2

|  | Core Particle Cellulose[2] | Shell Particle PMMA |
|---|---|---|
| Example 2 | 95 | 5 |
| Example 3 | 97.5 | 2.5 |

Cellulose[1]: Cellulobeads D-5 marketed by Daito Kasei in Japan
Cellulose[2]: Cellulobeads USF marketed by Daito Kasei in Japan
PMMA: Polymethylmethacrylate MP-2200 marketed by Soken in Japan

[Microscopic Observation]

The composite particle according to each of Examples 1-3 was visually observed by scanning electron microscopy, and it was confirmed that the shell particles were attached on the surface of the core particle, and that a part of the surface of the core particle was exposed (the entire surface of the core particle was not covered by the shell particles). No free shell particles were found.

[Stabilization of O/W Interface]

For each of Tests 1-3 and Controls 1-3, 0.1 g of each powder in Table 3 shown below was mixed with 8 g of water. The obtained mixture was shaken by hand. Next, 2 g of hydrogenated polyisobutene was added to the mixture. The obtained mixture was further shaken by hand.

TABLE 3

| | Powder |
|---|---|
| Test 1 | Composite Particle of Example 1 |
| Test 2 | Composite Particle of Example 2 |
| Test 3 | Composite Particle of Example 3 |
| Control 1 | Cellulose[1] |
| Control 2 | Cellulose[2] |
| Control 3 | Silica (and) Methicone |

Cellulose[1]: Cellulobeads D-5 marketed by Daito Kasei in Japan
Cellulose[2]: Cellulobeads USF marketed by Daito Kasei in Japan
Silica (and) Methicone: Porous silica beads coated with polymethylhydrogenpolysiloxane The mixtures according to Tests 1-3 and Controls 1-3 thus obtained were left at room temperature for 2 months. The aspect of each mixture was visually evaluated.

In case of Tests 1-3, an O/W emulsion phase was formed in the mixture. The O/W emulsion phase in each of Tests 1-3 did not change even after 2 months, and therefore, the O/W emulsion phase was found to be stable.

On the other hand, no O/W emulsion phase was formed in the mixture in case of Controls 1 and 2.

In the case of Control 3, an O/W emulsion phase was formed in the mixture. However, 2 months later, a part of the oil was separated and found on the top of the emulsion phase. Thus, the O/W emulsion phase was found to be unstable.

The above test results (Tests 1-3) show that the composite particles according to Examples 1-3 can stabilize the O/W interface, due to a combination of the hydrophilic core particle (cellulose) and hydrophobic shell particles (PMMA), wherein the surface of the composite particle has hydrophilic and hydrophobic regions.

The above test results also show that the hydrophilic core particle alone has no amphiphilic property to stabilize the O/W interface (Controls 1 and 2), and that the hydrophilic particle (silica) wherein at least a part of the surface of the hydrophilic particle has been chemically hydrophobicized by use of covalent bonding with polymethylhydrogensiloxane (the surface of the hydrophilic particle is not partially covered with hydrophobic particles) can only show inferior stabilization effects for the O/W interface (Control 3), as compared to the composite particle based on a combination of a hydrophilic core particle and hydrophobic shell particles wherein the surface of the hydrophilic core particle is partially covered with hydrophobic particles (Examples 1-3).

Examples 4-5

The components shown in the table below (Table 4) were subjected to a mechanochemical fusion process using mechanochemical fusion equipment equipped with a high-speed rotor having a plurality of blades in a chamber in dry conditions, to obtain a composite particle.

In detail, for each of Examples 4-5, the components shown in Table 4 were mixed at the mixing ratio (the numerals in Table 4 are based on parts by weight) shown in Table 4 in a plastic bag by shaking by hand for a short period of time. The mixture was put in the mechanochemical fusion equipment, and the rotor was rotated at 32.5 m/s (linear velocity) for 20 minutes to obtain the composite particle according to each of Examples 4-5.

TABLE 4

|  | Hydrophilic Particle Cellulose[1] | Hydrophobic particles | |
|---|---|---|---|
|  |  | Crosslinked Styrene/ acrylate copolymer | $TiO_2$ |
| Example 4 | 20 | 50 | 30 |
| Example 5 | 30 | 40 | 30 |

Cellulose[1]: Cellulobeads D-5 marketed by Daito Kasei in Japan
Hydrophobic particles: Cross-linked Styrene/acrylate copolymer SUNSPHERES marketed by Dow. $TiO_2$: MT-100TV marketed by Tayca in Japan.

[Microscopic Observation]

The composite particle according to each of Examples 4-5 was visually observed by scanning electron microscopy, and it was confirmed that hydrophobic particles were attached on the surface of the hydrophilic particle, and that a part of the surface of the hydrophilic particle was exposed

[Optical Effect Measurement: Haze and Transparency]

Light scattering and transparency are two important characteristics for potential ingredients in make-up blurring formulae. Those properties are measured quite often by using a Hazemeter. This apparatus enables the measurement of Transmission, T, and Haze value, H, (also called scattered or diffused transmission) of different kind of samples. For the purpose of describing the optical potential for cosmetics preparations, the materials of Examples 4-5 were analyzed using the following protocol: 10 g of a conventional O/W skincare formula were prepared by mixing 0.3 g of each powder in table 4 and 9.7 g of the base with the composition detailed below (conventional O/W skincare base formula).

TABLE 5

| Ingredients: | wt % |
|---|---|
| GLYCERYL STEARATE (and) PEG-100 STEARATE | 3 |
| PEG-40 STEARATE | 3 |
| CETYL ALCOHOL | 1.2 |
| STEARYL ALCOHOL | 1.2 |
| HYDROGENATED POLYISOBUTENE | 6 |
| AQUA | 65.68 |
| PHENOXYETHANOL | 0.6 |
| CAPRYLYL GLYCOL | 0.6 |
| ISOHEXADECANE | 18 |
| CARBOMER | 0.36 |
| TRIETHANOLAMINE | 0.36 |

The measurement with formulae comprising Examples 4-5 were compared to the measurement with formulae with no composite particle (control). The results below (Table 6) demonstrate that the composite particles according to Examples 4-5 can provide haze effect superior to control with very limited alteration of transparency.

TABLE 6

| Sample | Description | T | H |
|---|---|---|---|
| Control | Formula with no composite particle | 92.1 | 6.2 |
| Example 6 | Formula comprising composite particle described in Example 4 | 88.9 | 87.6 |
| Example 7 | Formula comprising composite particle described in Example 5 | 89.8 | 72.3 |

The invention claimed is:

1. A composite particle comprising:
   at least one hydrophilic and water-insoluble core particle comprising at least one porous cellulose; and
   a plurality of hydrophobic shell particles comprising at least one polymer selected from poly(meth)acrylates, polyalkyl(meth)acrylates, styrene/acrylate copolymers, cross-linked styrene/acrylate copolymers, or combinations thereof,
   wherein the surface of the at least one hydrophilic and water-insoluble core particle is substantially discontinuously covered by the hydrophobic shell particles, and an uncovered hydrophilic surface of the at least one hydrophilic and water-insoluble core particle is present,
   wherein the at least one hydrophilic and water-insoluble core particle and the plurality of hydrophobic shell particles are present in a weight ratio ranging from about 20:80 to about 30:70.

2. The composite particle according to claim 1, wherein the hydrophilic and water-insoluble core particle and hydrophobic shell particles have a polarity difference wherein $\Delta E = E_T(30)$ hydrophilic core particle $- E_T(30)$ hydrophobic shell particles greater than about 2.

3. The composite particle according to claim 1, wherein the mean particle size of the hydrophilic and water-insoluble core particle ranges from about 100 nm to about 200 µm.

4. The composite particle according to claim 1, wherein at least about 90 vol % of the hydrophilic and water-insoluble core particle has a mean primary particle size ranging from about 2 to about 7 µm.

5. The composite particle according to claim 1, wherein the ratio of the longest diameter to the shortest diameter of the hydrophilic and water-insoluble core particle ranges from about 1.0 to about 2.5.

6. The composite particle according to claim 1, wherein the ratio of the wet point for water to the wet point for oil is about 5 or less.

7. The composite particle according to claim 1, wherein the mean particle size of the hydrophobic shell particles ranges from about 10 nm to about 100 µm.

8. The composite particle according to claim 1, wherein from about 10 to about 90% of the surface of the hydrophilic and water-insoluble core particle is covered by the hydrophobic shell particles.

9. A composition comprising at least one composite particle comprising:
   at least one hydrophilic and water-insoluble core particle comprising at least one porous cellulose; and
   a plurality of hydrophobic shell particles comprising at least one polymer selected from poly(meth)acrylates, polyalkyl(meth)acrylates, styrene/acrylate copolymers, cross-linked styrene/acrylate copolymers, or combinations thereof,
   wherein the surface of the at least one hydrophilic and water-insoluble core particle is substantially discontinuously covered by the hydrophobic shell particles, and an uncovered hydrophilic surface of the at least one hydrophilic and water-insoluble core particle is present,
   wherein the at least one hydrophilic and water-insoluble core particle and the plurality of hydrophobic shell particles are present in a weight ratio ranging from about 20:80 to about 30:70.

10. The composition according to claim 9 further comprising a physiologically acceptable medium.

11. A non-therapeutic cosmetic process for caring for and/or making up a keratin material, the process comprising:
    applying to the surface of the keratin material at least one composition comprising at least one composite particle comprising:
    at least one hydrophilic and water-insoluble core particle comprising at least one porous cellulose; and
    a plurality of hydrophobic shell particles comprising at least one polymer selected from poly(meth)acrylates, polyalkyl(meth)acrylates, styrene/acrylate copolymers, cross-linked styrene/acrylate copolymers, or combinations thereof,
    wherein the surface of the at least one hydrophilic and water-insoluble core particle is substantially discontinuously covered by the hydrophobic shell particles, and an uncovered hydrophilic surface of the at least one hydrophilic and water-insoluble core particle is present,
    wherein the at least one hydrophilic and water-insoluble core particle and the plurality of hydrophobic shell particles are present in a weight ratio ranging from about 20:80 to about 30:70.

12. A method for preparing a composite particle, comprising a step of subjecting:
- at least one hydrophilic and water-insoluble core particle comprising at least one porous cellulose; and
- a plurality of hydrophobic shell particles comprising at least one polymer selected from poly(meth)acrylates, polyalkyl(meth)acrylates, styrene/acrylate copolymers, cross-linked styrene/acrylate copolymers, or combinations thereof, to a mechanochemical fusion process,
- wherein the surface of the at least one hydrophilic and water-insoluble core particle in the composite particle is substantially discontinuously covered by the hydrophobic shell particles, and an uncovered hydrophilic surface of the at least one hydrophilic and water-insoluble core particle is present,
- wherein the at least one hydrophilic and water-insoluble core particle and the plurality of hydrophobic shell particles are present in a weight ratio ranging from about 20:80 to about 30:70.

13. The method according to claim 12, wherein the mechanochemical fusion process is a hybridizer process.

14. The composite particle according to claim 1, wherein the hydrophilic and water-insoluble core particle has:
- a wet point for oil of at least about 25 ml/100 g, and
- a wet point for water of at least about 50 ml/100 g.

15. The composite particle according to claim 1, wherein the hydrophilic and water-insoluble core particle has:
- a wet point for oil of about 35 ml/100 g to about 600 ml/100 g, and
- a wet point for water of about 100 ml/100 g to about 600 ml/100 g.

16. The composite particle according to claim 1, wherein the hydrophilic and water-insoluble core particle has:
- a wet point for oil of about 40 ml/100 g to about 500 ml/100 g, and
- a wet point for water of about 150 ml/100 g to about 500 ml/100 g.

17. The composite particle according to claim 1, wherein the ratio of the wet point for water to the wet point for oil of the hydrophilic and water-insoluble core particle is about 5 or less.

* * * * *